US00PP37397P2

(12) United States Plant Patent
Boxriker

(10) Patent No.: US PP37,397 P2
(45) Date of Patent: Apr. 28, 2026

(54) ***DAHLIA* PLANT NAMED 'KLEDH24695'**

(50) Latin Name: ***Dahlia* sp.**
Varietal Denomination: KLEDH24695

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/348,525

(22) Filed: Oct. 2, 2025

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new *Dahlia* plant designated 'KLEDH24695' particularly distinguished by dark pink flowers with a purple eye; weak filling; and a semi-upright plant habit. is disclosed.

1 Drawing Sheet

Genus and species: *Dahlia* sp.
Variety denomination: 'KLEDH24695'.

BACKGROUND

The present invention comprises a new and distinct variety of *Dahlia*, botanically known as *Dahlia* sp., and hereinafter referred to by the variety name 'KLEDH24695'. 'KLEDH24695' originated from a controlled cross with the female proprietary 'DH-2018-5603' (unpatented) and the proprietary male parent 'DH-2017-4265' (unpatented) in autumn 2019 in Stuttgart, Germany. In April 2020 a seedling was selected and named 'KLEDH24695'. 'KLEDH24695' was first vegetatively propagated by vegetative cuttings in May 2020 in Latina, Italy. 'KLEDH24695' was found to reproduce true to type in successive generations of asexual propagation.

SUMMARY

The following are the most outstanding and distinguishing characteristics of 'KLEDH24695' when grown under normal horticultural practices in Latina, Italy.

1. Dark pink flowers with a purple eye;
2. Weak filling; and
3. Semi-upright plant habit.

DESCRIPTION OF THE PHOTOGRAPH

This new *Dahlia* plant is illustrated by the accompanying photograph of the plant approximately fourteen weeks old and grown in a greenhouse in Stuttgart, Germany. The photograph shows the whole plant, unless otherwise noted, including the inflorescences and foliage and buds and was taken in May 2024 in Stuttgart, Germany. The colors shown are as true as can be reasonably obtained by conventional photographic procedures.

DESCRIPTION OF 'KLEDH24695'

The following detailed descriptions set forth the distinctive characteristics of 'KLEDH24695'. The data which define these characteristics were collected from asexual reproductions carried out in Latina, Italy. Data was collected on 16-week-old plants, with one pinch and grown in a greenhouse. Color references are to The R.H.S. Colour Chart of The Royal Horticultural Society of London (R.H.S.), 5$^{th}$ edition (2007).

Classification:
- *Family*.—Asteraceae.
- *Botanical*.—*Dahlia* sp.
- *Designation*.—'KLEDH24695'.

Parentage:
- *Female parent*.—'DH-2018-5603' (unpatented).
- *Male parent*.—'DH-2017-4265' (unpatented).

Propagation:
- *Type*.—Vegetative terminal cuttings.
- *Time to produce a rooted young plant*.—3 to 4 weeks.
- *Time to produce a flowering plant*.—About 10 weeks.
- *Root description*.—RHS N155C in color, fine.
- *Rooting habit*.—Freely branching and moderately dense.

Plant description:
- *Plant and growth habit*.—Semi-upright.
- *Plant height*.—To the top of foliar plane: About 22.0 cm. Including inflorescence: About 27.0 cm.
- *Plant diameter*.—About 33.0 cm.

Lateral branches:
- *Length*.—Up to the last pair of leaves: About 13.0 cm. Including inflorescence: About 22.0 cm.
- *Diameter*.—About 0.35 cm.
- *Internode length*.—About 2.8 cm.
- *Strength*.—Medium strong.
- *Texture*.—Smooth.
- *Color*.—Close to RHS N77A.

Foliage description:
- *Arrangement*.—Opposite.
- *Length*.—*About* 12.5 cm.
- *Width*.—Up to 5.0 cm for the simple foliage, up to 8.5 cm for the pinnate foliage.
- *Shape*.—Ovate.
- *Apex*.—Acute.

*Base*.—Acute.
*Margin*.—Serrate.
*Venation pattern*.—Pinnate.
*Venation color*.—Close to RHS 144A at the time and RHS N77A at the base with a mix of both colors along the length of the leaf.
*Texture*.—Upper and lower surface: Little hairy on the edges, slightly rugose and glossy.
*Color*.—Immature: Upper surface: Close to RHS 137A. Lower surface: Close to RHS 138B. Mature: Upper surface: Close to RHS N137B. Lower surface: Close to RHS 191B.

Petioles:
*Length*.—About 3.5 cm for the simple foliage, about 4.0 cm for the pinnate foliage.
*Diameter*.—About 0.3 cm.
*Texture*.—Upper surface: Smooth. Lower surface: Smooth.
*Color*.—Upper surface: Close to RHS 146B to RHS N77A. Lower surface: Variable but close to RHS 144A at the base to RHS N77A at the tip to RHS 146C with a mixture of the three colors along the length of the petiole.

Inflorescence description:
*Appearance and arrangement*.—Composite head inflorescence, daisy eyed, held above the foliage.
*Fragrance*.—Not detected.
*Time to flower*.—About 10 weeks after potting.
*Post-production longevity*.—Plants flower continuously from spring through autumn.

Inflorescence bud:
*Height*.—About 1.2 cm.
*Diameter*.—About 1.5 cm.
*Shape*.—Globular.
*Color*.—Close to RHS 146B.

Inflorescence size:
*Diameter*.—About 6.5 cm.
*Depth (height)*.—About 4.3 cm.
*Disc diameter*.—About 1.0 cm.
*Receptacle height*.—About 0.4 cm.
*Receptacle diameter*.—About 1.0 cm.
*Receptacle color*.—Close to RHS 144A.

Ray florets:
*Quantity per inflorescence*.—About 75.
*Length*.—About 2.8 cm.
*Width*.—About 1.4 cm.
*Shape*.—Elliptic.
*Apex*.—Pointed.
*Base*.—Fused in a tube.
*Margin*.—Entire.
*Aspect*.—Keeled.
*Texture*.—Upper surface: Smooth. Lower surface: Smooth.
*Color*.—Immature: Upper surface: Tone close to RHS 59A but darker and shiny. Lower surface: Close to RHS 59A. Mature: Upper surface: Close to RHS 59A and close to RHS N78B at the distal quarter. Lower surface: Close to RHS 59A to RHS 59B, and close to RHS 77D at the distal quarter.

Disc florets:
*Quantity per inflorescence*.—35.
*Length*.—About 0.9 cm.
*Diameter*.—About 0.15 cm.
*Shape*.—Tubular.
*Texture*.—Inner surface: Smooth. Outer surface: Smooth.
*Color*.—Immature and mature: Inner and outer surface: Close to RHS 1A (yellow) with red/brown shade at the tips, some completely red burgundy (close to tone 59A but much darker).

Phyllaries:
*Quantity per inflorescence*.—5 at the external whorl, about 14 in the internal whorls.
*Length*.—About 1.2 cm the external ones, about 1.5 cm the inner ones.
*Width*.—About 0.4 cm.
*Shape*.—Lanceolate to spatulate.
*Apex*.—Broadly acute.
*Base*.—Attenuate the external ones, fused the internal whorls.
*Margin*.—Entire.
*Texture*.—Upper surface: Smooth and slightly glossy. Lower surface: Smooth and slightly glossy.
*Color*.—Upper surface: external whorl: Close to RHS 137B. internal whorl: RHS 144A at the base with RHS 145C at the tips. Lower surface: external whorl: RHS 137A. internal whorl: RHS 144A at the base with RHS145C at the tips.

Peduncles:
*Length, terminal peduncle*.—About 6.0 cm.
*Length, axillary peduncle*.—Up to 9.0 cm.
*Diameter*.—About 0.2 cm.
*Strength*.—Medium strong.
*Texture*.—Smooth.
*Color*.—Close to RHS N77A.

Reproductive organs:
*Androecium*.—Quantity per floret: 5 stamens with fused anthers (central with 12). Filament length: About 0.18 cm. Filament color: Close to RHS 1A. Anther shape: Oblong. Anther length: 0.3 cm. Anther color: RHS 23A. Pollen amount: Abundant. Pollen color: RHS 23A.
*Gynoecium*.—Only on disc florets. Quantity per floret: 1. Pistil length: 0.9 cm. Style length: About 0.3 cm. Style color: Close to RHS 1A. Stigma shape: Bipartite. Stigma color: Close to RHS 2A. Ovary color: RHS 149D.

Fruit and seed set: Not observed.

Disease and pest/insect resistance: No disease resistance observed.

COMPARISON OF 'KLEDH24695' WITH PARENTAL LINES AND KNOWN VARIETY

'KLEDH24695' is distinguished from the parents as described in Table 1.

TABLE 1

Comparison with Parental Lines

| Trait | Variety 'KLEDH24695' | Female parent | Male parent |
|---|---|---|---|
| Flower color | Dark pink with a purple eye | White with pink stripes | Pink-magenta |

'KLEDH24695' can be compared to the commercial *Dahlia* variety 'KLEDH24691' (U.S. Plant Patent Application pending). Differences between the varieties are described in Table 2.

TABLE 2

| Comparison with Similar Variety | | |
|---|---|---|
| Trait | Variety 'KLEDH24695' | Commercial line 'KLEDH24691' |
| Flower color | Dark pink with a purple eye | Magenta with a dark eye |

TABLE 2-continued

| Comparison with Similar Variety | | |
|---|---|---|
| Trait | Variety 'KLEDH24695' | Commercial line 'KLEDH24691' |
| Flower filling | Weaker than 'KLEDH24691' | Stronger filling than 'KLEDH24965' |

I claim:

1. A new and distinct variety of *Dahlia* plant designated 'KLEDH24695', as illustrated and described herein.

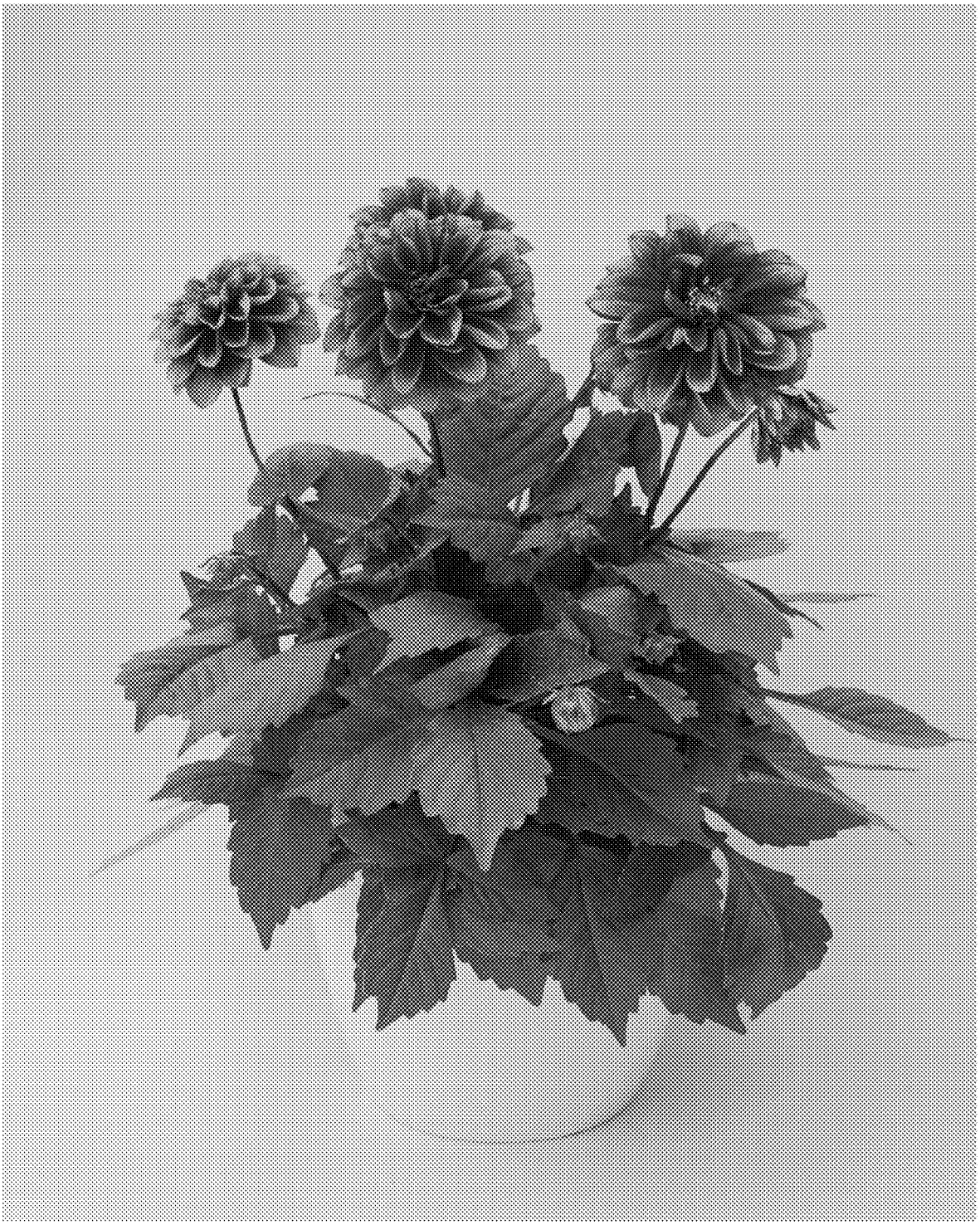

* * * * *